United States Patent [19]

Trautmann et al.

[11] Patent Number: 4,473,491
[45] Date of Patent: Sep. 25, 1984

[54] ALKANOLAMINE SALTS OF CYCLIC AMIDE ACIDS AND THEIR USE AS METAL CORROSION INHIBITORS IN AQUEOUS SYSTEMS

[75] Inventors: Walter Trautmann, Neustadt; Elmar Getto, Mannheim, both of Fed. Rep. of Germany

[73] Assignee: BASF Aktiengesellschaft, Ludwigshafen, Fed. Rep. of Germany

[21] Appl. No.: 387,743

[22] Filed: Jun. 11, 1982

[30] Foreign Application Priority Data

Jun. 22, 1981 [DE] Fed. Rep. of Germany ....... 3124402

[51] Int. Cl.³ ............................................. C09K 3/00
[52] U.S. Cl. .................................... 252/392; 252/33.6; 252/34; 252/49.5; 252/51.5 A; 106/14.15; 106/14.18; 106/14.42; 422/16; 260/501.16; 260/501.17; 260/464; 260/465 D; 560/41; 560/118; 560/120; 560/122; 560/125
[58] Field of Search ............... 252/392, 33.6, 34, 49.5, 252/515 A; 106/14.15, 14.18, 14.42; 422/16; 260/501.17, 501.16, 465 D, 464; 560/41, 120, 118, 122, 125

[56] References Cited

U.S. PATENT DOCUMENTS

| | | | |
|---|---|---|---|
| 2,339,796 | 1/1944 | Musher | 252/392 X |
| 3,095,286 | 6/1963 | Andress, Jr. et al. | 252/392 X |
| 3,224,969 | 12/1965 | Hotten | 252/392 X |
| 3,897,349 | 7/1975 | Marin et al. | 252/34 X |
| 4,207,285 | 6/1980 | Oppenlaender et al. | 422/16 |
| 4,259,206 | 3/1981 | Piotrowski et al. | 252/51.5 A X |
| 4,273,664 | 6/1981 | Brandolesz | 252/49.5 |
| 4,289,636 | 9/1981 | Davis et al. | 252/49.5 X |
| 4,289,636 | 9/1981 | Davis et al. | 252/51.5 A X |
| 4,344,862 | 8/1982 | Widder et al. | 252/180 X |
| 4,379,063 | 5/1983 | Williams | 252/392 X |
| 4,388,199 | 6/1983 | Brandolese | 252/392 X |
| 4,425,248 | 1/1984 | Piotrowski et al. | 252/49.5 X |

Primary Examiner—Benjamin R. Padgett
Assistant Examiner—Matthew A. Thexton
Attorney, Agent, or Firm—David L. Hedden

[57] ABSTRACT

Alkanolamine salts of amide acids having the formula:

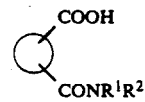

in which the circle represents a single nucleous aromatic ring or a monocyclic or bicyclic aliphatic ring system in each case with 5 or 6 carbon atoms per ring in which $R^1$ represents an isoalkyl radical with the longest chain of 6 to 8 carbon atoms and a total of 8 to 12 carbon atoms; $R^2$ represents a radical alkylene-X wherein the alkylene chain is a branched or straight chain and contains 1 to 4 carbon atoms; X represents $OR^3$, $O(C_2H_4O)_n\text{-}R^3$, $O(C_3H_6O)_n\text{-}R^3$, $NR^3R^3$, $CN$, $CONH_2$, and $COOR^3$; $R^3$ represents hydrogen or $C_1$ to $C_4$ alkyl; n is an integer of 1 to 4; and wherein the carboxyl and carbonamide groups in said formula are bonded to non-olefinic carbon atoms and arranged in adjacent positions. The use of these salts as corrosion inhibitors in aqueous systems is also disclosed.

18 Claims, No Drawings

ALKANOLAMINE SALTS OF CYCLIC AMIDE ACIDS AND THEIR USE AS METAL CORROSION INHIBITORS IN AQUEOUS SYSTEMS

BACKGROUND OF THE INVENTION

1. Field of the Invention

The invention relates to alkanolamine salts of cyclic amide acids as metal corrosion inhibitors in aqueous systems.

2. Description of the Prior Art

Technical processes which take place in the presence of water always involve the problem of corrosion protection if corrosion endangered metals such as iron, aluminum, zinc, copper or their alloys are involved in these processes such as cleaning processes, the use of cooling water or cooling lubricants as well as hydraulic fluids. With such process media the additional problem of pronounced foaming is incurred particularly in those cases where substances with surfactant properties are present as corrosion inhibitors. To date this problem could only be solved by added foam inhibitors which when they did not disturb the mentioned processes rendered them less economical.

German published application No. 2,758,123 describes alkanolamine salts of maleic-N-($C_8$- to $C_{12}$)-alkyl amide acids by means of which these problems can be solved if the salts are present in the process medium in low concentrations. U.S. Pat. No. 2,378,442 describes calcium salts of N-alkylated phthalamide acids as rust inhibiting lubricating oil additives, and U.S. Pat. No. 3,095,286 describes cyclic amide acids as corrosion inhibitors. However, in accordance with the above-mentioned literature references, these compounds are oil- but not water-soluble, and they are used only as additives in lubricating oil or fuels.

Certain applications, for instance, when contact corrosion between various metals is to be prevented such as in metal cutting, require higher concentrations of inhibitors in order to provide sufficient corrosion protection. For metal cutting such as drilling, threading, milling, sawing or grinding of material pieces, the low foaming property of the process medium is of particular importance. For such higher concentrations, the maleic amide acid salts disclosed in the above-mentioned literature reference are not effective in control of foam.

The goal of this invention is to provide substances which do not foam even in higher concentrations while otherwise providing at least equal corrosion protection as compared to prior art corrosion inhibitors. Surprisingly, the goal of the invention was reached with alkanolamine salts of cyclic amide acids as further described below.

SUMMARY OF THE INVENTION

According to this invention, it has been found that the alkanolamine salts of cyclic amide acids are low foaming in aqueous systems and provide very good corrosion protection. The useful amide acids have the formula:

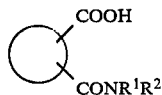

in which the circle represents a single nucleous aromatic ring or a monocyclic or bicyclic aliphatic ring system in each case with 5 or 6 carbon atoms per ring in which $R^1$ represents an isoalkyl radical with the longest chain of 6 to 8 carbon atoms and a total of 8 to 12 carbon atoms; $R^2$ represents a radical alkylene-X wherein the alkylene chain is a branched or straight chain and contains 1 to 4 carbon atoms; X represents $OR^3$, $O(C_2H_4O)_n$-$R^3$, $O(C_3H_6O)_n$-$R^3$, $NR^3R^3$, CN, $CONH_2$, and $COOR^3$; $R^3$ represents hydrogen of $C_1$ to $C_4$ alkyl; n is an integer of 1 to 4; and wherein the carboxyl and carbonamide groups in said formula are bonded to non-olefinic carbon atoms and arranged in adjacent positions. The use of these salts as corrosion inhibitors in aqueous systems is also disclosed.

DETAILED DESCRIPTION OF THE INVENTION

The use of cyclic amide acids as alkanolamine salts and thus in a water soluble form may appear obvious. It has been found, however, that, depending on the length of the chain and the structure of the longer alkyl radical bonded to the amide nitrogen there results either substances which foam too much (if the chain is too long) or which are almost water insoluble. In addition, if the chain is too short or, in case of an n-alkyl chain without branches, the corrosion inhibition effect is greatly reduced. It is the narrow range of the chain length and the isomerization degree according to this invention which provide the desired properties as well as reduced electrolyte sensitivity.

It was noted that the alkanolamine salts of amide acids having formula I provide greatly reduced anticorrosive effect when $R^1$ represents an n-octyl- radical or a lower n-alkyl radical. If $R^1$ stands for isoalkyl, the reduction in the anticorrosive effect occurs when the radicals have less than 8 carbon atoms. With too great a number of carbon atoms in the longest chain of the isoalkyl radical (>8), the foam development is excessive.

The amide acid salts used in accordance with this invention are derived from the reaction of cyclic amide acids and alkanolamines. Useful amide acids are those in which the carboxylic acid and carbonamide groups are in adjacent positions and the carbon atoms carrying these groups are not olefinic. These are obtained, for instance, by reacting the corresponding cyclic acid anhydrides of formula:

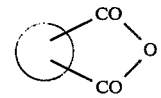

in which the circle is defined above under formula I with the amines of formula:

in which $R^1$ and $R^2$ are also defined above under formula I.

The ring of the anhydrides of formula II can be a single nucleous aromatic ring, for instance a benzene ring, which can be substituted by $C_1$ to $C_4$ alkyl groups, fluorine, chlorine, bromine atoms, nitro groups or carboxyl groups. The ring also can be aliphatic, namely mono- or bi-cyclic, in which case 5 or 6 carbon atoms are present per ring. Possible ring systems are the cyclopentane, cyclopentene, cyclohexane, cyclohexene, the bicyclo-[2,2,1]-heptane or heptene or bicyclo-[2,2,2]-octane or octene. In this case also, the above-mentioned substituents are possible.

As preferred anhydrides one may choose at least one of phthalic acid anhydride, tetrahydrophthalic acid anhydride, hexahydrophthalic acid anhydride or bicyclo-[2,2,1]-hept-2-en-5,6-dicarboxylic anhydride as starting compounds.

Amines having formula III, which react with such anhydrides, are secondary amines where $R^2$ represents the radical alkylene-X. The alkylene radical may contain 1 to 4 carbon atoms and may be a straight chain or branched chain if it contains 3 to 4 carbon atoms. X represents a functional group, such as $OR^3$, $O(C_2H_4O)_nR^3$, $O(C_3H_6O)R^3$, CN, $CONH_2$, $COOR^3$ and $N(R^3)_2$ and $R^3$ denotes hydrogen or $C_1$- to $C_4$ alkyl. Primary amines from which the abovementioned substituted amines are derived include at least one of isooctylamines, isononylamines, isodecylamines, isoundecylamines and isododecylamines all of which have 6 to 8 carbon atoms in the longest chain. Isooctylamines and isononylamines are preferred.

In order to arrive at the amines of formula III, the primary amines can be reacted with 1 to 4 moles of at least one alkylene oxide selected from the group consisting of ethylene oxide and propylene oxide and the resultant alkoxylates are optionally etherified with at least one of $C_1$ to $C_4$ alcohols such as ethanol or isopropanol. One mole of ethylene oxide or propylene oxide is used on a preferred basis. In addition to this, the primary amines also can be reacted in a basically well known fashion with acrylonitrile, acrylamide, acrylic acid or $C_1$ to $C_4$ alkyl esters of acrylic acid to result in the corresponding N-(2'-cyano-ethyl)-, N-(2-carbon amido-ethyl)-, N-(2-carbomethoxyethyl)- or N-(2'-carboxy-ethyl)-amines. Furthermore, the primary amines also can be reacted with at least one of halogenated alkane carboxylic acids, carboxylic acid nitriles, amides, or esters with 1 to 4 carbon atoms per halogenated alkane group resulting in the corresponding (N-cyanoalkyl, carboamidoalkyl, carboalkoxylalkyl, and carboxylalkyl) amino compounds. The reaction of primary amines with at least one of crotonic acid or methacrylic acid, their esters, amides or nitriles also can result in amines having formula III. A last group of formula III amines is represented by the amines of formula III where $R^2$ represents alkylene-X, wherein X represents $N(R^3)_2$, namely, N-(2'-Di-$C_1$-$C_4$ amino alkyl amines. In all cases, the substituted N-isooctyl- and isononylamines are particularly preferred.

These amines may be used as mixtures with corresponding N-substituted straight chain $C_8$ to $C_{12}$ alkyl amines in such an amount that the later end products contain up to 90 percent by weight based on the alkanolamine salt of the corresponding n-alkylamide acid salts.

The reaction of the anhydrides with the amines can take place in accordance with commonly used methods which do not require any specific explanations. The resultant amide acids are subsequently neutralized with the alkanolamines in accordance with basically known methods. In order to achieve a liquid consistency, up to 25 percent by weight of water may be added to the resultant salts.

The "alkanolamine" compounds useful in this invention are selected from the group consisting of said compounds which are capable of forming water-soluble salts, that is, primarily the $C_1$ to $C_4$ alkanolamines, the N-$C_1$ to $C_4$ alkyl, $C_2$ to $C_4$ alkanolamines, and mixtures thereof. Individual specific representatives of these substances include mono-, di-, or triethanolamines, isopropanolamine or N-methyl-mono-, di-ethanol-, isopropanolamine. Finally, alkanolamines derived from alkoxylated ethylene diamine such as four-fold ethoxylated or propoxylated ethylene diamine may also be used. N-(2'-hydroxyethyl)-N-(2-ethylhexyl)- as well as the N-(2'-cyanoethyl)-N(2-ethylehexyl)-monoamides of phthalic acid anhydride and of tetrahydrophthalic acid anhydride which have been neutralized with triethanolamine or diethanolamine have been found to be particularly effective inhibitors.

These salts of the invention are corrosion inhibitors which have been found to be highly effective in preventing foaming in aqueous systems even at increased concentrations. Depending upon the application, said salts are added to the process media in amounts of 0.01 to 5 percent by weight based on the amount of medium.

The corrosion inhibitors of the invention were evaluated using the corrosion tests described below:

HERBERT CORROSION TEST

The corrosion protection effect is illustrated by using an aqueous solution containing 1 and 2 percent of the active substance and various degrees of water hardness using the Herbert Test System which is used in the metal processing industry. This system consists of a standardized cast iron plate and also standardized steel shavings having a length of 5 mm which are supplied by the Alfred Herbert Company in Coventry, England. The square plate having dimensions of $100 \times 100 \times 5$ mm is ground prior to the test using a belt grinder with a 120 Korundum grinding belt. The plate is then washed with gasoline and ethanol and is dried with a clean cloth.

Following this, the steel shavings which are supplied with the test system and which are produced from 0.40 percent carbon steel under standardized conditions are placed on the prepared cast iron plate using a suitable metal or plastic spoon which has the volume of approximately a normal teaspoon in such a manner that 4 small heaps are placed on the cast iron plate so that they are equidistant from each other and to the edges of the plate. The shavings should be arranged in a single layer and as close to each other as possible.

The solutions and/or emulsions which are to be tested as to their corrosion behavior are placed on the shaving heaps by way of a measuring pipette and in such amounts that the liquid reaching the cast iron plate is just barely held together by the shavings. After 24 hours in an atmosphere having a relative humidity of 70 percent, the shavings are removed from the plate by tipping the latter. The definitely visible outline of the dried-on aqueous medium remains. At the contact points of the shavings with the plate, rust spots of various sizes have formed depending upon the corrosive nature of the liquid. These spots may also represent a cohesive layer. The evaluation is facilitated by visual estimation of the percentage area of rust.

CAST IRON FILTER PAPER TEST

Another corrosion test consists in the so-called cast iron filter paper test. A Petri dish with an ID of approximately 10 cm with a fitting cover is used for this test. A round black band filter is placed in the Petri bowl. Using a suitable spoon, 5 to 10 grams of coarse cast iron GG-20-shavings are distributed over the filter in such a manner that a uniform pile is created in the center of the filter at a distance of approximately 1.5 cm from the edge. The shavings are approximately 5 to 8 mm long and must be obtained from clean cast iron GG-20 material without use of drilling oil or other cooling lubricants. All fine particles must be removed by screening. Using a measuring pipette, 5 ml of the solution or emulsion to be tested for its corrosiveness are in each case uniformly placed on the shavings. The pH value of the test fluid is determined since it is of significance for the evaluation. It can be adjusted to a certain standard value, for instance 8.5. After applying the test liquid, the cover is placed on the Petri dish and the test materials are allowed to stand for 2 hours under normal lab conditions at 23° C. to 25° C. and approximately 70 percent relative humidity. After this, the cover is removed, the filter is briefly upturned and is placed on the surface of tap water thereby removing the shavings. Immediately thereafter, the filter paper is sprayed and saturated with an indicator solution of the following composition:

1 gram calcium hexacyanoferrate (III)
30 grams sodium chloride
1 liter water

After allowing the indicator to work for 17 seconds in air, the filter is carefully rinsed under running drinking water and is then dried in air at a moderately warm place. After this procedure, and depending upon the corrosiveness of the medium, brownish-yellow, yellow and/or blueish-yellow spots of varying intensity will develop on the filter paper with the brownish-yellow or yellow color being less advantageous than the other mentioned colors. Flawless behavior is indicated by the lack of any brown or yellow coloration and perhaps traces of blueish-green pale spots. The filters are totally color stable and may, therefore, serve as controls.

An evaluation scale may be as follows:
(— —) very poor: bright, large predominantly yellow-brown spots
(—) poor: bright, large spot with approximately equal yellow-brown and blue-green portions
(+ —) medium: pale medium sized spots with approximately equal yellow and blue-green portions
(+) good: very pale, small (pin size) spots or medium sized spots which are of a predominantly blue-green color
(+ +) very good: no spots or no more than very few, very small pale blue-green spots.

The beating method was used according to DIN 53 902. For the test the simple testing method sufficed where the stamp with a perforated plate is uniformly moved up and down by hand 30 times in 30 seconds and is then carefully removed (IG beating method). The foam volume is read off in milimeters using the graduated foam cylinder after 1, 5 and 10 minutes. In addition to this, the data concerning temperature, concentration and water hardness are of importance.

While this invention has been described with reference to certain specific embodiments, it will be recognized by those skilled in the art that many variations are possible without departing from the scope and spirit of the invention, and it will be understood that it is intended to cover all changes and modificatioins of the invention disclosed herein for the purposes of illustration which do not constitute departure from the spirit and scope of the invention.

The following examples illustrate the various aspects of the invention but are not intended to limit its scope. Where not otherwise specified throughout this specification and claims, temperatures are given in degrees centigrade and parts, percentages and proportions are by weight.

EXAMPLE 1

While stirring at 80° C., 148 grams (1 mole) of phthalic anhydride as a hot melt at 170° C. there was dripped into said anhydride 173 grams (1 mole) of N-(2'-hydroxyethyl)-2-ethylhexylamine (boiling point 1.5 mbar/92° C. to 93° C.). The temperature was increased to 100° C. and was maintained at this temperature by controlling the feed. After feed is completed, the mixture was stirred at 80° C. for 1 hour. The resultant phthalamide acid solidifies in a glass-like manner at room temperature and has an acid number of 179 (theoretical 175).

There were stirred together 40.6 parts by weight of phthalamide acid, 50.5 parts by weight of triethanolamine, and 8.9 parts by weight of diethanolamine at 60° C. to 80° C. until a clear liquid was obtained. In a 1 percent aqueous solution this mixture has a pH value of 8.8.

EXAMPLE 2

The phthalamide acid was prepared as described in Example 1. 56.8 parts by weight of triethanolamine were added to 43.2 parts by weight of this phthalamide acid and the materials are thereupon mixed at 60° C. to 80° C. until a clear liquid results. A 1 percent aqueous solution of this mixture had a pH value of 8.4.

EXAMPLE 3

Preparation of N-(2'-cyanoethyl)-2-ethylhexlamine

While stirring at 20° C., 55.7 grams (1.05 moles) of acrylonitrile were dripped into 129 grams (1 mole) of 2-ethylhexylamine for a period of 20 minutes. The temperature was increased to 30° C. The mixture was stirred at 100° C. for 2 hours and was subsequently degassed at 50° C. under a high vacuum for 1 hour. The remaining residue was 172 grams (=93 percent of theory) of liquid N-(2'-cyanoethyl)-2-ethylhexylamine. The 60 MHz-NMR spectrum (m 2.9 ppm; m 2.5 ppm; 0.7 to 1.5 ppm) confirms the structure.

Preparation of Phthalamide Acid

At 100° C., 101 grams (0.68 mole) of phthalic anhydride as a 140° C. hot melt was dripped into 124 grams (0.68 mole) N-(2'-cyanoethyl)-2-ethylhexylamine in such a manner that the internal temperature does not increase beyond 110° C. At room temperature the phthalamide acid solidified in a glass-like manner and analyzed as follows: IR COOH; C=N at 2240; 1710; 1590; 770 cm$^{-1}$, acid number 178 (theoretical 170).

Preparation of the Triethanolamine Salt

There were stirred 35 parts by weight of this phthalamide acid and 65 parts by weight of triethanolamine at 60° C. to 80° C. until a clear liquid results. In a 1 percent aqueous solution, the mixture had a pH value of 8.5.

EXAMPLE 4

Preparation of N-(2'-carbomethoxy-ethyl)-2-ethylhexylamine

While stirring at a temperature of 20° C., 90.3 grams (1.05 mole) of methylacrylate were dripped into 129 grams (1 mole) of 2-ethylhexylamine within a period of 30 minutes. The temperature was increased to 35° C. The mixture was stirred at 100° C. for 2 hours and was subsequently degassed at 50° C. under a high vacuum for 1 hour. The remaining residue was 210 grams (98 percent of theory) liquid N-(2'-carbomethoxy-ethyl)-2-ethylhexylamine. The 60 MHz-Nuclear Magnetic Resonance Spectrum s 3.7 ppm COOCH$_3$; m 2.9 ppm; m 2.5 ppm; 0.7 to 1.5 ppm confirms the structure.

PREPARATION OF PHTHALAMIDE ACID

There were heated 165 grams (0.77 mole) N-(2'-carbomethoxy-ethyl)-2-ethylhexylamine to 100° C. and 114 grams (0.77 mole) phthalic anhydride were slowly added by dripping as a 140° C. melt so that the temperature was increased to a maximum of 110° C. After cooling to room temperature, the phthalamide acid solidifies in a glass-like manner which analyzed as follows:

IR: COOH; 1720; 1590; 770 m$^{-1}$
NMR: s 3.75 ppm COOCH$_3$.

Preparation of the Triethanolamine Salt

There were stirred 41.2 parts by weight of this phthalamide acid with 58.8 parts by weight of triethanolamine at 60° C. to 80° C. until a clear liquid results. In a 1 percent aqueous solution, the mixture had a pH value of 8.3.

EXAMPLE 5

There were heated 187 grams (1 mole) N-(2'-hydroxy-propyl)-2-ethylhexylamine to 80° C. While stirring, 148 grams (1 mole) phthalic anhydride were dripped in as a 170° C. melt while the temperature of the reaction mixture was maintained at 100° C. After feed is completed, the mixture was stirred at 80° C. for 1 hour.

The product had an acid number of 170 (theoretical 167).

There were stirred together 42 parts by weight of this phthalamide acid, 49.3 parts by weight of triethanolamine, and 8.7 parts by weight of diethanolamine at 60° C. to 80° C. until a clear liquid results. In a 1 percent aqueous solution the mixture had a pH value of 8.5.

EXAMPLE 6 (CONTROL)

Phthalic acid-mono-isoamyl-amide as triethanolamine salt.

EXAMPLE 7 (CONTROL)

Phthalic acid-mono-n-octyl-amide as triethanolamine salt.

EXAMPLE 8 (CONTROL)

Phthalic acid-mono-o-toluidide as triethanolamine salt.

EXAMPLE 9 (CONTROL)

Phthalic acid-mono-di-(2-ethylhexyl)amide as triethanolamine salt.

EXAMPLE 10 (CONTROL)

Phthalic acid-mono-tridecylamide as triethanolamine salt.

EXAMPLE 11 (CONTROL)

Maleic acid-mono-2-ethylhexyl-amide as triethanolamine salt in accordance with German published application No. 2,758,123.

In addition to the products according to this invention mentioned in Examples 1–5, a number of other amide acids are used for comparison purposes in Examples 6–11. This facilitates showing the narrow range of compositions needed to obtain the simultaneous occurrence of the desired properties which represent the objective of this invention. Control Example 11 shows the most advanced state of the art, which this invention exceeds, particularly in the low foaming properties (3 percent solution). In the test results which follow in Table I, particular attention should be given to the foam stability, that is, the foam volume after 10 minutes.

TABLE I

| | | Foaming and Corrosion Performance | | | | | |
|---|---|---|---|---|---|---|---|
| | | Foaming Behavior (Beating Method, 3% Distilled Water, Room Temperature) Foam Volume in Milimeters | | | Herbert Test, area % rust | | |
| | Concentrate (Concentration of salt in water) | after 1 min. | after 5 min. | after 10 min. | 1% in 10° d (drinking water) | 2% in 23° d (drinking water) | 2% in 20° d according to DIN 52360 |
| Invention | | | | | | | |
| Example 1 | 100% | 80 | 40 | 40 | 0 | 0 | 5 |
| Example 2 | 100% | 120 | 50 | 50 | 0 | 5 | 5 |
| Example 3 | 100% | 100 | 50 | 40 | 0 | 5 | 5 |
| Example 4 | 100% | 250 | 70 | 50 | 1 | 2 | 5 |
| Example 5 | 100% | 200 | 80 | 50 | 0 | 0 | 0 |
| Controls | | | | | | | |
| Example 6 | 90.2% | 0 | 0 | 0 | 100 | 50 | 50 |
| Example 7 | 85.0% | 350 | 190 | 120 | 5 | 10 | 15 |
| Example 8 | 92.5% | 0 | 0 | 0 | 90 | 40 | 100 |
| Example 9 | 100% | 1300 | 1300 | 1200 | 5 | 10 | 25 |
| Example 10 | 100% | 550 | 550 | 450 | 10 | 30 | 15 |
| Example 11 | 100% | 470 | 390 | 200 | 0 | 0 | 0 |

TABLE II

| | Cast Iron Filter Paper Corrosion Test | | | | |
|---|---|---|---|---|---|
| | 1% in 10° d (drinking water) | 2% in 23° d (drinking water) | 2% in 20° d according to DIN 51360 | pH value (1% in water) | Appearance of the 1% solution in distilled water |
| Invention | | | | | |
| Example 1 | ++ | ++ | ++ | 8.8 | almost clear |
| Example 2 | ++ to + | ++ | + | 8.4 | almost clear |
| Example 3 | ++ to + | ++ to + | + | 8.5 | transparent |
| Example 4 | ++ to + | + | + | 8.3 | transparent |
| Example 5 | ++ | ++ | ++ to + | 8.5 | almost clear |
| Controls | | | | | |
| Example 6 | +− | + to +− | +− | 8.5 | almost clear |
| Example 7 | | ++ to + | + | 8.4 | cloudy |
| Example 8 | − | +− | − | 8.5 | almost clear |
| Example 9 | + | ++ to + | + | 8.5 | cloudy |
| Example 10 | +− | + to +− | +− | 8.5 | cloudy |
| Example 11 | + to +− | ++ | ++ | 8.5 | almost clear |

The embodiments of the invention in which an exclusive privilege or property is claimed are defined as follows:

1. Alkanolamine salts of cyclic amide acids, which are water soluble, low foaming, corrosion inhibitors, wherein said amide acids have the formula

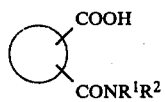   I in which the circle represents a single nucleus aromatic ring or a monocyclic or bicyclic aliphatic ring system having 5 or 6 carbon atoms per ring in which $R^1$ represents an isoalkyl radical with the longest chain having 6 to 8 carbon atoms and a total of 8 to 12 carbon atoms; $R^2$ represents a radical alkylene-X wherein the alkylene chain is a branched or straight chain and contains 1 to 4 carbon atoms; X represents $OR^3$, $O(C_2H_4)_nR^3$, $O(C_3H_6O)_n-R^3$, $NR^3R^3$, CN, $CONH_2$ and $COOR^3$; $R^3$ respresents hydrogen or $C_1$ to $C_4$ alkyl; n is an integer of 1 to 4; and wherein the carboxyl and carbonamide groups in said formula are bonded to non-olefinic carbon atoms and arranged in adjacent positions.

2. The salt of claim 1 wherein said amide acids are derived from the reaction of a cyclic acid anhydride of the formula:

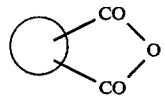   II with amines of the formula:

   III wherein $R^1$ and $R^2$ are defined in claim 1.

3. The salt of claim 2 wherein said anhydrides of formula II contain a single nucleous aromatic ring.

4. The salt of claim 3 wherein said aromatic ring is a benzene ring substituted with substitutents selected from the group consisting of at least one of $C_1$ to $C_4$ alkyl, flourine, chlorine, bromine, nitro, and carboxyl groups.

5. The composition of claim 2 wherein said monocyclic or bicyclic aliphatic ring in said cyclic acid anhydrides of formula II is selected from the group consisting of cyclopentane, cyclopentene, cyclohexane, cyclohexene, the bicyclo-[2,2,1]-heptane or heptene and the bicyclo-[2,2,2]-octane or octene.

6. The salt of claims 4 or 5 wherein said anhydride is selected from the group consisting of phthalic acid anhydride, tetrahydrophthalic acid anhydride, hexahydrophthalic acid anhydride, and bicyclo-[2,2,1]-hept-2-en-5,6-dicarboxcylic anhydride and mixtures thereof.

7. The salt of claim 2 wherein said amines of formula III are prepared by reacting primary amines having 6 to 8 carbon atoms with a reactant selected from the group consisting of an alkylene oxide, acrylonitrile, acrylamide, acrylic acid or $C_1$ to $C_4$ alkyl esters thereof, halogenated alkane carboxylic acids, carboxylic acid nitriles, carboxylic acid amides, or carboxylic acid esters having 1 to 4 carbon atoms per halogenated alkane group, crotonic acid, methacrylic acid, or the esters, amides, or nitriles of crotonic acid and methacrylic acid and mixtures thereof.

8. The salt of claim 7 wherein said primary amines are selected from the group consisting of isooctylamines, isononylamines, isodecylamines, isoundecylamines, isododecylamines and mixtures thereof.

9. The salt of claim 8 wherein said primary amines are isooctylamines or isononylamines.

10. The salt of claim 7 wherein said primary amines are reacted with 1 to 4 moles of alkylene oxide selected from the group consisting of at least one of ethylene oxide and propylene oxide to produce a primary amine-alkylene oxide reaction product.

11. The salt of claim 10 wherein said primary amine-alkylene oxide reaction product is reacted with $C_1$ to $C_4$ alcohols selected from the group consisting of at least one of ethanol and isopropanol.

12. The salt of claim 11 wherein said primary amine-alkylene oxide reaction product is etherified with 1 mole of ethylene oxide or 1 mole of propylene oxide.

13. The salt of claim 2 wherein said alkanolamine salts are derived from alkanolamines which are water-soluble salts of said amide acids.

14. The salt of claim 13 wherein said alkanolamines are selected from the group consisting of the $C_1$ to $C_4$ alkanolamines, the N-$C_1$ to $C_4$ alkyl, $C_2$ to $C_4$ alkanolamines, and mixtures thereof.

15. The salt of claim 14 wherein said alkanolamines are selected from the group consisting of mono-, di-, and triethanolamines; isopropanolamine; N-methylmono-, diethanol-, isopropanol- amine and mixtures thereof.

16. The salts of claim 14 wherein said alkanolamines are derived from alkoxylated ethylene diamine.

17. The salt of claim 14 wherein said alkanolamine salts of amide acids are selected from the group consisting of N-(2'-hydroxyethyl)-N-(2-ethylhexyl)-and the N-(2'-cyanoethyl)-N-(2-ethylhexyl)- monoamides of phthalic acid anhydride or tetrahydrophthalic acid anhydride which have been neutralized with triethanolamine or diethanolamine.

18. The process of inhibiting the corrosion of metal by an aqueous liquid comprising adding to said liquid an alkanol amine salt of a cyclic amide acid having the salt defined by claim 2.

* * * * *